United States Patent
Calvet et al.

(10) Patent No.: US 9,194,813 B2
(45) Date of Patent: Nov. 24, 2015

(54) METHOD AND DEVICE FOR THE AUTOMATIC INSPECTION OF A CABLE SPOOL

(75) Inventors: Marc Calvet, Clermont-Ferrand (FR); Jean-Paul Zanella, Clermont-Ferrand (FR); Davy Vernier, Beaumont (FR)

(73) Assignees: COMPAGNIE GENERALE DES ETABLISSEMENTS MICHELIN, Clermont-Ferrand (FR); Michelin Recherche et Technique S.A., Granges-Paccot (CH)

( * ) Notice: Subject to any disclaimer, the term of this patent is extended or adjusted under 35 U.S.C. 154(b) by 201 days.

(21) Appl. No.: 13/500,690

(22) PCT Filed: Oct. 4, 2010

(86) PCT No.: PCT/EP2010/064737
§ 371 (c)(1),
(2), (4) Date: Sep. 21, 2012

(87) PCT Pub. No.: WO2011/042386
PCT Pub. Date: Apr. 14, 2011

(65) Prior Publication Data
US 2013/0051652 A1    Feb. 28, 2013

(30) Foreign Application Priority Data
Oct. 6, 2009   (FR) ...................................... 09 56947

(51) Int. Cl.
G06K 9/00   (2006.01)
G01N 21/88  (2006.01)
G01N 21/952 (2006.01)

(52) U.S. Cl.
CPC .......... *G01N 21/8851* (2013.01); *G01N 21/952* (2013.01)

(58) Field of Classification Search
CPC ................. G06T 7/0004; G06T 7/001; G06T 2207/30148; G06T 2207/30164; G06T 7/0006
USPC ................................... 382/141, 149; 356/625
See application file for complete search history.

(56) References Cited

U.S. PATENT DOCUMENTS

2001/0037694 A1    11/2001  Freifeld
2011/0069323 A1*    3/2011  Takahashi et al. ............ 356/625

FOREIGN PATENT DOCUMENTS

FR    2 925 198     6/2009
JP    07-92105      4/1995
(Continued)

OTHER PUBLICATIONS

Matsushima, an English machine translation of JP2008-203149, 2008.*

*Primary Examiner* — Ruiping Li
(74) *Attorney, Agent, or Firm* — Cozen O'Connor

(57) ABSTRACT

Method for detecting and evaluating the protrusions that appear on cords coming from a twisting/rubberizing process, by the digital processing of the image of a layer of cord formed by a number of turns wound around the core of a spool (4), which method comprises the steps during which: A) the raw digital image of the surface of the layer of cord over one complete revolution of the spool is taken using a linear camera (1); B) the raw image is displayed flat so as to limit the influence of the variations in lighting and in the brightness of the wires; C) the flattened image is segmented so as to reveal the dark areas that contain protrusion areas; D) the segmented image is a processed using a series of morphological processing operations in order to separate and select the shapes likely to represent protrusions and areas likely to represent shadows; and E) an evaluation value is assigned to the final image obtained and the evaluation value is compared with a threshold value.

8 Claims, 4 Drawing Sheets

(56) References Cited

FOREIGN PATENT DOCUMENTS

| JP | 07-167797 | 7/1995 |
| JP | 2001-041726 | 2/2001 |
| JP | 2008-139201 | 6/2008 |
| JP | 2008-203149 | 9/2008 |
| JP | 2009-008502 | 1/2009 |

* cited by examiner

METHOD AND DEVICE FOR THE AUTOMATIC INSPECTION OF A CABLE SPOOL

RELATED APPLICATIONS

This is a U.S. National Phase Application under 35 USC §371 of International Application PCT/EP2010/064737, filed on Oct. 4, 2010.

This application claims the priority of French application no. 09/56947 filed on Oct. 6, 2009, the content of which is hereby incorporated by reference.

FIELD OF THE INVENTION

The invention relates to the field of the manufacture of reinforcing cords intended mainly for the tire industry.

BACKGROUND OF THE INVENTION

These cords, of textile or metallic nature, are usually employed in the manufacture of tires in the form of plies containing mutually parallel threads or wires and making an angle in relation to the circumferential direction, or bundles of cords, which are deposited directly on the tire blank during production. The cords are obtained by combining individual threads or wires that are assembled together in successive layers and twisted so as to give the final cord the desired mechanical strength and elasticity properties.

The invention relates to cords, essentially metal cords, in which a rubber compound is injected between the layers of wire so as to give the cord additional wear resistance and corrosion resistance properties. The cords are obtained by a combination of assembling and rubberizing means so that the rubber compound is trapped within the structure of the cord.

A process of this type is described for example in the publication WO 2005/071157.

However, it turns out that, during implementation of this process, elements of rubber compound remain on the surface of the cords. These protrusions present on the surface of the cords constitute undesirable aggregates because of the disturbance that they introduce into the downstream cord production processes. Furthermore, they constitute localized areas of additional thickness of compound on the back of the reinforcing cords, and make it more difficult to control the thicknesses of rubber compound deposited on these cords during the calendaring operations.

The publication WO 2009/083213 describes for example an improved process which makes it possible to reduce the protrusions in question in a cord of 3+N type. In remoter technological fields, the publication FR 2 925 198 describes a method and a device for checking the proportion of hydrides present in a metal alloy, such as an alloy used for cladding nuclear fuel rods, and comprising image processing means, but the construction thereof is not appropriate to solving the problem addressed. Likewise, the publication US 2001/0037694 describes a method of checking the wall thickness of stents used in medical applications, which also involves image processing means for selecting the measurement areas.

SUMMARY OF THE INVENTION

One aspect of the invention is to provide an inspection method for ensuring, by automatic inspection means, that the cords produced comply with the specifications.

Cable inspection takes place on the spool onto which the cords, coming from the twisting/rubberizing process, are wound.

The method according to one aspect of the invention relates to image processing steps and comprises the following steps during which:

A the raw digital image of the surface of the layer of cord over one complete revolution of the spool is taken using a linear camera;

B the raw image is displayed flat so as to limit the influence of the variations in lighting and in the brightness of the wires;

C the flattened image is segmented so as to reveal the dark areas that contain protrusion areas;

D the segmented image is a processed using a series of morphological processing operations in order to separate the shapes likely to represent protrusions and areas likely to represent shadows; and E an evaluation value is assigned to the final image obtained and the evaluation value is compared with a threshold value.

In this way, an assessment of the manufactured quality is obtained slightly later, enabling the operators to adjust the parameters governing the rubberizing/twisting process, thereby eliminating evaluation variations due to the wavering in the attention of the operators carrying out a visual check.

Using a classifying grid, it is also possible, once the spool has been filled, to assign an overall evaluation value to the spool of cord and to send said spool to one of the circuits in the manufacturing process.

BRIEF DESCRIPTION OF THE DRAWINGS

The description that follows is based on FIGS. 1 to 10 in which.

DETAILED DESCRIPTION OF THE DRAWINGS

Figure 1:
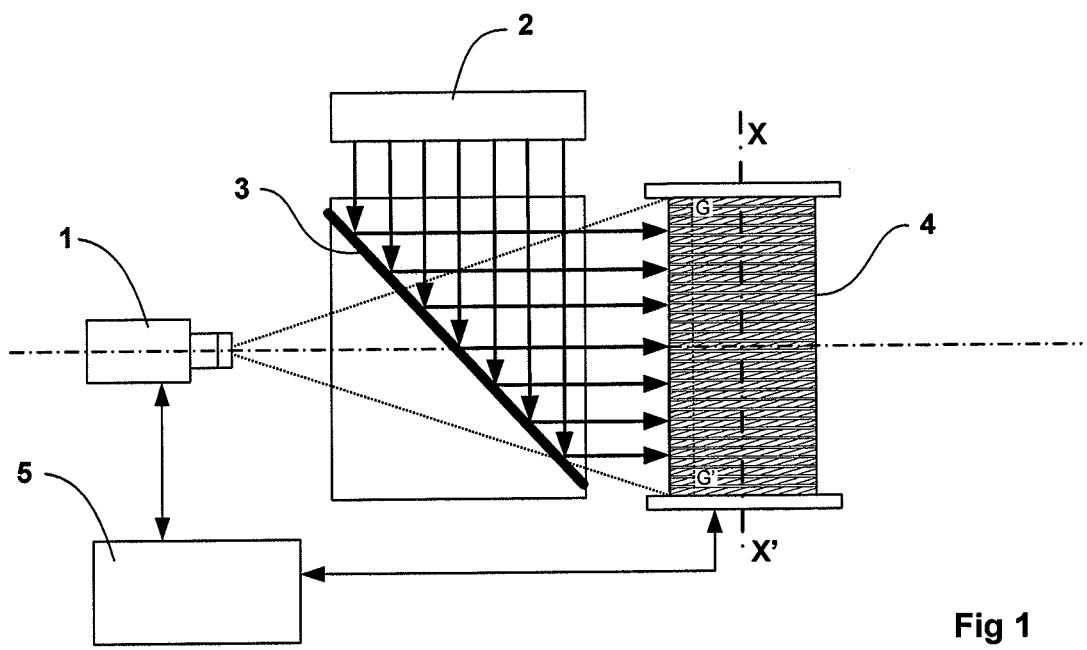
FIG. 1 shows a schematic view of the evaluation device.

FIG. 1 shows the device for taking an image and for processing it.

A linear camera 1 takes an image of a generatrix GG' of the cylinder formed by the layer of cord comprising a number of turns wound around the core XX' of the spool 4, coming from the rubberizing and the twisting processes (not shown).

An illumination means of coaxial type emits a collimated light beam toward a semi-reflecting plate 3. A line of light-emitting diodes can usefully be used as illumination means. The semi-reflecting plate 3 directs the light beam toward the spool 4 of wire.

The device further includes a digital processing means 5 for processing the digital image generated by the camera 1. The power of this processing means is suitable for being able to carry out digital transformations on the image, such as those described in the following paragraphs.

The following description details all the steps carried out for detecting and evaluating the size and number of the protrusions present on a layer of turns.

Figure 2:
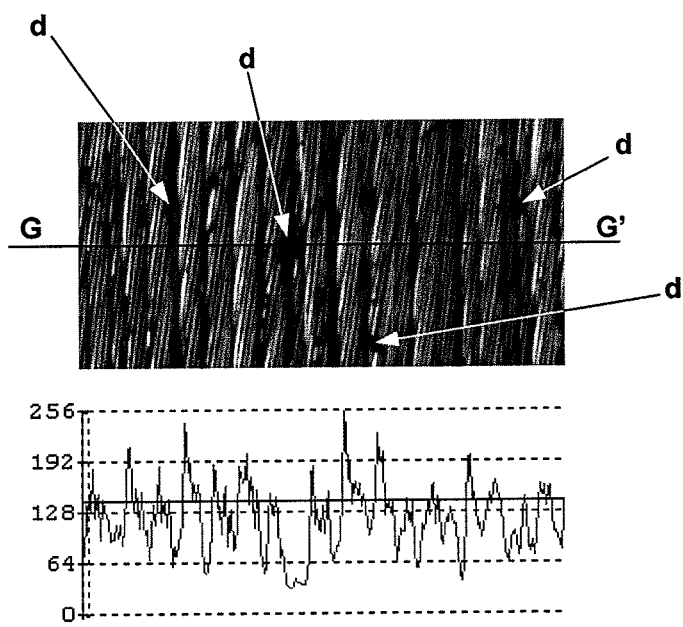
FIG. 2 shows the raw image of the developed surface of a layer of wire.

Adding the linear images produced by the camera 1 over one revolution of the spool gives a digital image representing the developed surface of a layer of turns, as illustrated by FIG. 2.

The diagram shows the grey level recorded by the camera along a generatrix GG', the x-axis representing the generatrix GG' and the y-axis representing the grey level (the value 0 being attributed to the colour black).

The arrows pinpoint the undesirable protrusions d observed visually on the product by an operator. These protrusions are distinguished in general from the shadows cast on the wires in that the shadows have a generally elongate shape, whereas said protrusions have a shape with no pronounced elongation along a preferential direction.

The aim of the image processing method is to distinguish the protrusions from the other dark spots visible on the image, these consisting of the shadow areas located preferentially between the wires.

The first step of the method according to the invention, called the flattening-out step, consists in rendering the image independent of the light level of the illumination source and of overly bright spots. This operation is similar to the use of a low-pass analogue filter.

Figure 3:
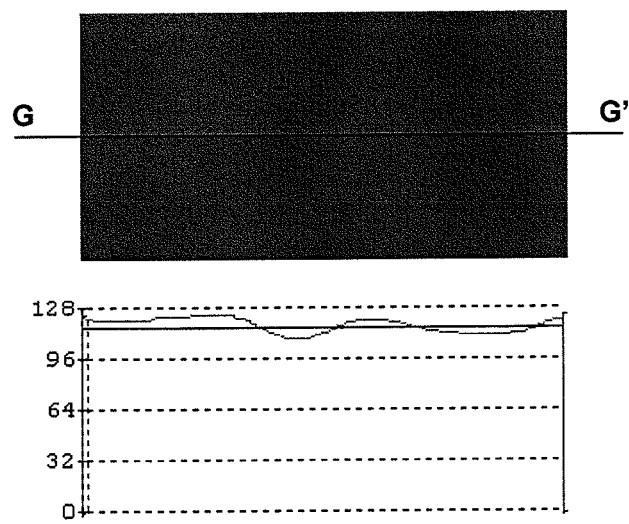
FIGS. 3 and 4 show the images obtained during the flattening-out step.
Figure 4:
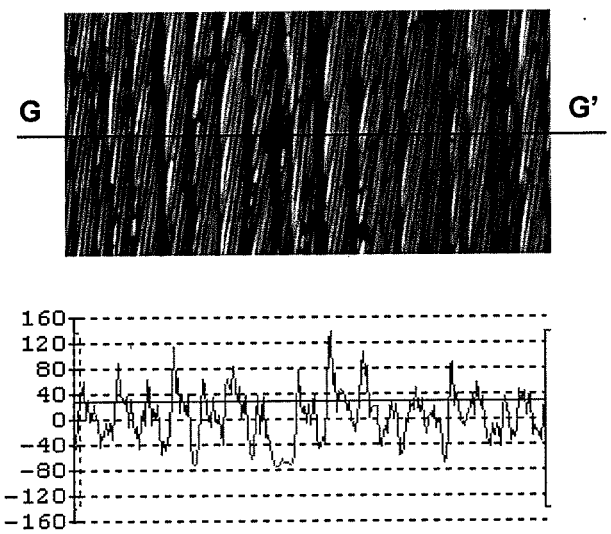

For this purpose each pixel of the image is assigned the average of the grey level of the surrounding pixels (see FIG. 3) and this value is subtracted from the grey level of the raw image of the original pixel. The image resulting from this first image processing step is illustrated in FIG. 4.

Figure 5:
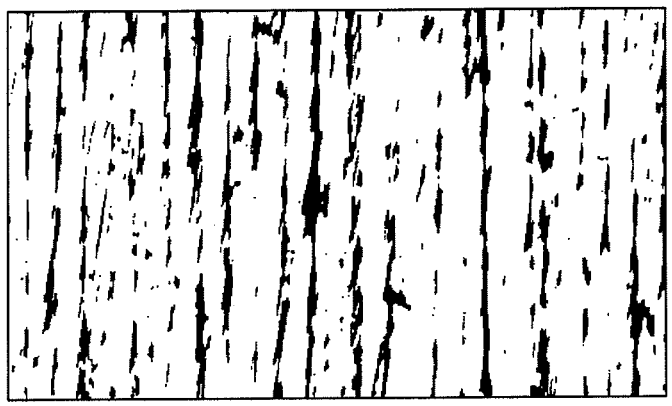
FIG. 5 shows the image obtained after the segmentation step.

The next step consists in segmenting the flattened-out image resulting from the previous step, so as to obtain a black-and-white image as shown in FIG. 5, in which the pixels having a grey level above a threshold value have a white colour, a black colour being assigned to those pixels whose grey level is below this threshold.

The threshold value is calculated according to the dispersion of the grey levels of the flattened-out image resulting from the first step.

The following step consists in carrying out a series of what are called morphological processing operations, so as to distinguish the generally elongate shapes, which are revealed as shadows, from the other shapes that are less extended in a preferential direction, which are revealed as protrusions.

Figure 6:
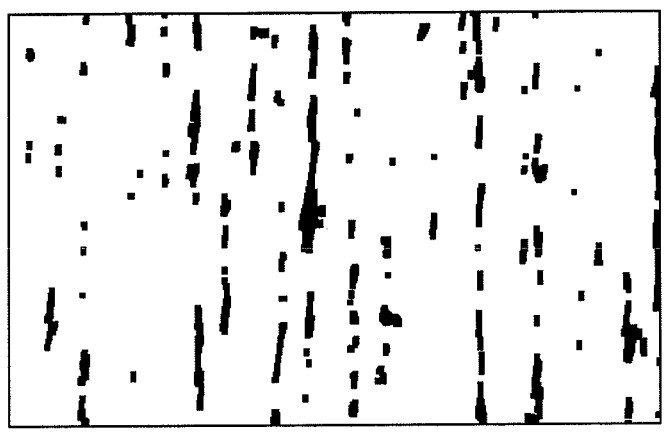
FIGS. 6, 7, 8, 9 and 10 show the images obtained during the various morphological processing steps.

To do this, a first image processing operation is carried out by performing a morphological opening operation using a structuring element of square shape, the size of which is determined experimentally in relation to the resolution of the image and the size of the smallest protrusions that it is desired to reveal. The mathematical algorithms for carrying out this operation are described for example in the work by Jean Serra "Image Analysis and Mathematical Morphology", Academic Press, London, 1982. This operation has the effect of eliminating asperities in the contour of the black areas and makes it possible to separate the more compact areas likely to represent protrusions from the more or less pronounced shadow areas essentially present between the wires. The image obtained after this processing operation is shown in FIG. 6.

It is possible to add to this first morphological opening processing operation a second transformation, called a distance transformation, after which the fine or elongate objects and the small-sized shapes are identified. To do so, the grey level is varied from the contour towards the interior of the black areas in increasing increments, going towards white on penetrating further into the interior of said area.

Figure 7:
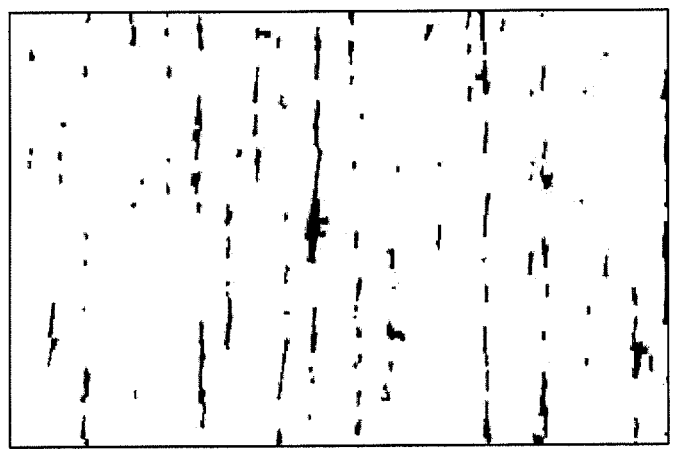

The large areas which are spread out identically in all directions (see FIG. 7) will have at their centre an area lighter than the narrow or small areas.

Figure 8:
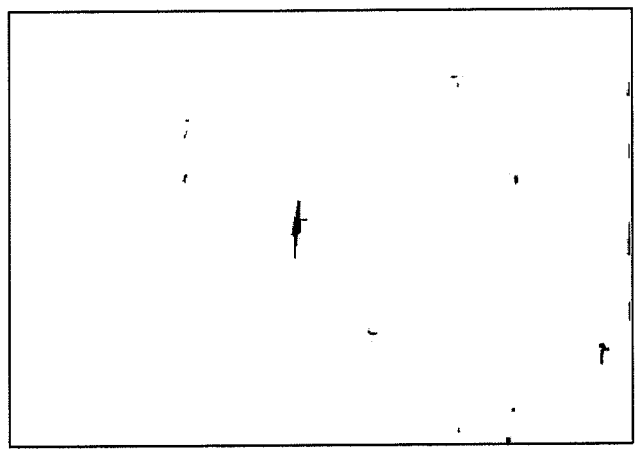
Figure 9:
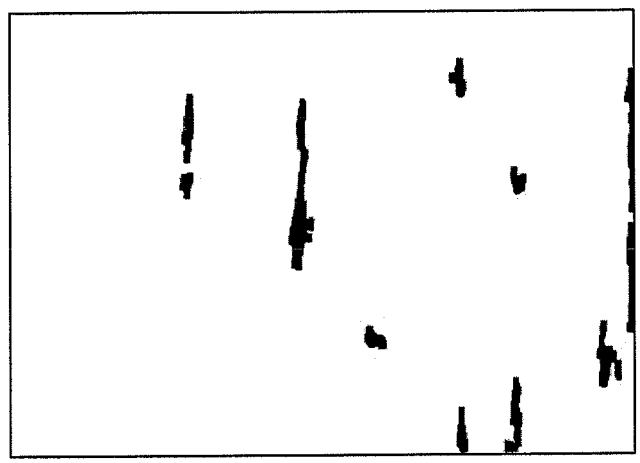

It is then sufficient to eliminate the areas having a minimum grey level below a given threshold in order to identify and select the large and slightly elongate areas (see FIG. 8). These areas are then reconstructed in their original form, as shown in FIG. 9.

The final processing step consists in applying a shape criterion, by calculating, for each of the remaining shapes, an aspect ratio equal to the ratio of the maximum length to the minimum width. In practice, this threshold is equal to 2.2 or higher.

The shapes having a higher ratio than a given threshold value are identified as being elongate areas, revealed as shadows, and these are eliminated.

Figure 10:
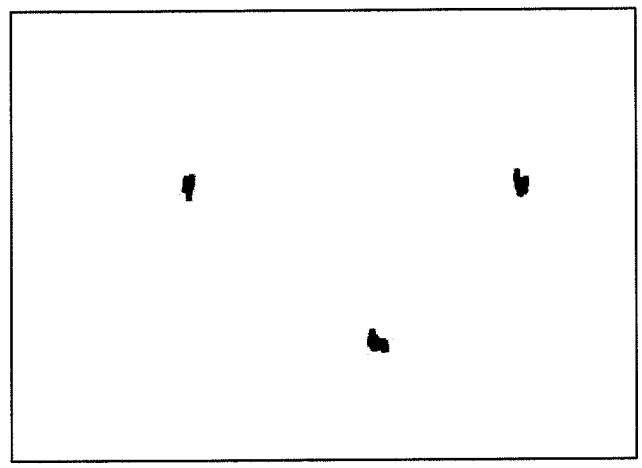

The remaining shapes are therefore revealed as protrusions, as illustrated in FIG. 10.

Referring again to the original image shown in FIG. 2, it may be seen that three of the four protrusions have been identified by the image processing software. The protrusion placed directly in contact with a shadow area was eliminated by mistake.

The final step of the digital processing consists in applying an evaluation value to the image obtained, counting the area and number of the detected protrusions, and putting these values into an evaluation table drawn up beforehand.

Depending on the evaluation grid it is possible, if desired, to trigger an alarm, to provide the operator responsible for adjusting the rubberizing and the twisting process parameters with a numerical figure, or else to determine, based on a decision grid, the destination of the spool of wire obtained, for which a final evaluation value may be calculated by adding the evaluation values calculated for each of the layers of wire wound onto the core of the spool.

The invention claimed is:

1. A method for detecting and evaluating protrusions that appear on cords from a twisting/rubberizing process, by digital processing of an image of a layer of cord formed by a number of turns wound around a core of a spool, which method comprises:

illuminating the layer of cord formed by the number of turns wound around the core of the spool using a coaxial illumination device configured to emit a collimated light beam toward a semi-reflecting plate that directs said collimated light beam toward the spool;

A) taking a raw digital image of a surface of the layer of cord over one complete revolution of the spool using a linear camera;

B) displaying a flattened image of the raw digital image to limit an influence of variations in lighting and variations in a brightness of wires of the cord;

C) segmenting the flattened image to reveal dark areas that contain protrusion areas;

D) processing the segmented flattened image using a series of morphological processing operations to separate and select shapes likely to represent the protrusions and areas likely to represent shadows to produce a final image, whereby the protrusions that appear on cords from the twisting/rubberizing process are identified; and E) assigning an evaluation value to the obtained final image and comparing the evaluation value with a threshold value.

2. The method according to claim 1, wherein the image processing carried out in step D comprises a morphological opening operation using a structuring element of square shape, wherein most compact areas are likely to represent the protrusions of the shadow areas present between the wires.

3. The method according to claim 1, wherein the image processing carried out in step D comprises a distance transformation operation for identifying fine objects and objects of small size.

4. The method according to claim 1, wherein the areas likely to represent shadows are revealed as long narrow areas, the aspect ratio of which is higher than a given threshold.

5. The method according to claim 4, wherein the aspect ratio is equal to 2.2 or higher.

6. A device for detecting and evaluating protrusions that appear on cords coming from a twisting/rubberizing process, by a digital processing of an image of a layer of cord formed by a number of turns wound around a core of a spool, which device comprises:
- a linear camera capable of taking a digital image of a generatrix (GG') of a cylinder formed by said layer of cord;
- a coaxial illumination device configured to emit a collimated light beam toward a semi-reflecting plate which directs said collimated light beam toward the spool; and
- a digital processing means for processing the digital image generated by the linear camera, which means contains a program capable of carrying out the digital processing operations comprising:
- illuminating the layer of cord formed by the number of turns wound around the core of the spool with a collimated light beam;

A) taking a raw digital image of a surface of the layer of cord over one complete revolution of the spool using a linear camera;

B) displaying a flattened image of the raw digital image to limit an influence of variations in lighting and variations in a brightness of wires of the cord;

C) segmenting the flattened image to reveal dark areas that contain protrusion areas:

D) processing the segmented flattened image using a series of morphological processing operations to separate and select shapes likely to represent the protrusions and areas likely to represent shadows to produce a final image, whereby the protrusions that appear on cords from the twisting/rubberizing process are identified; and E) assigning an evaluation value to the obtained final image and comparing the evaluation value with a threshold value.

7. method according to claim 1, wherein the semi-reflecting plate is arranged between the linear camera and the spool.

8. The device according to claim 6, wherein the semi-reflecting plate is arranged between the linear camera and the spool.

* * * * *